United States Patent [19]

Burton et al.

[11] 4,046,516

[45] Sept. 6, 1977

[54] HYDROGEN FLUORIDE-CATALYZED ALKYLATION APPARATUS

[75] Inventors: Vance P. Burton, Arlington Heights; Michael Z. Mikulicz, Palatine, both of Ill.

[73] Assignee: UOP Inc., Des Plaines, Ill.

[21] Appl. No.: 645,122

[22] Filed: Dec. 29, 1975

[51] Int. Cl.² .................... B01J 1/00; C07C 3/54
[52] U.S. Cl. .................... 23/288 E; 260/683.45
[58] Field of Search ............ 23/288 E; 260/683.45; 260/683.46

[56] References Cited

U.S. PATENT DOCUMENTS

| 3,087,917 | 4/1963 | Scoggin | 23/288 E UX |
| 3,249,650 | 5/1966 | Fenske | 260/683.45 X |
| 3,426,095 | 2/1969 | Passley | 23/288 E X |
| 3,544,651 | 12/1970 | Chapman | 260/683.45 |
| 3,707,580 | 12/1972 | Anderson | 23/288 E X |
| 3,787,518 | 1/1974 | Anderson | 260/683.45 |
| 3,804,918 | 4/1974 | Henderson | 23/288 E X |
| 3,910,771 | 10/1975 | Chapman | 23/288 E |

*Primary Examiner*—Barry S. Richman
*Attorney, Agent, or Firm*—James R. Hoatson, Jr.; Robert W. Erickson; William H. Page, II

[57] ABSTRACT

A process and apparatus for the hydrogen fluoride-catalyzed alkylation of hydrocarbonaceous species, utilizing multiple reaction zones, in which the inventories and strengths of catalysts within the several reaction zones are controlled. A portion of the catalyst from a reaction zone over-abundant in either acid strength or acid inventory is educted from that zone and passed to a reaction zone deficient in either acid strength or acid inventory. The apparatus includes catalyst recycle conduits within each reaction-settling zone and conduit means for interconnecting the individual recycle conduits to provide alternative flow paths to move catalyst from one recycle conduit to another recycle conduit or vice-versa.

1 Claim, 2 Drawing Figures

HYDROGEN FLUORIDE-CATALYZED ALKYLATION APPARATUS

BACKGROUND OF THE INVENTION

1. Field of the Invention

The field of the art to which this invention pertains is that of hydrocarbon processing. In particular, this invention relates to an improved process for the hydrogen fluoride-catalyzed alkylation of hydrocarbonaceous compounds. This invention specifically relates to an improved apparatus for conducting hydrogen fluoride-catalyzed alkylation reactions.

2. Prior Art

Various catalytic compounds have been used in the art for the promotion of alkylation of hydrocarbon species. Of particular current interest are the products of alkylation of isoparaffins with olefins to produce antiknock motor fuels and the alkylation of aromatics with olefins to produce precursors of biodegradable detergent products. Catalysts which contain hydrogen fluoride as their essential active ingredient possess considerable advantage over other possible catalytic agents such as a metal halide with a halogen halide promoter, phosphoric acid, and sulfuric acid. For example, when using a hydrogen fluoride catalyst the alkylation reaction may be conducted at a substantially higher reaction rate than with sulfuric acid, while, at the same time producing less undesirable side reactions. The used hydrogen fluoride catalyst may be withdrawn from a processing zone and conveniently regenerated to produce purified hydrogen fluoride, which can be returned to the processing zone for reuse. A spent hydrogen fluoride catalyst commonly contains water and heavy hydrocarbonaceous polymers as well as hydrogen fluoride. Universal practice is to regenerate this spent acid by distillation, or more commonly by fractionation, of the spent acid to yield a stream of contaminants and a stream of relatively pure and anhydrous hydrogen fluoride. The return of this high-purity hydrogen fluoride to the process has presented problems where the process contains multiple reaction zones.

Multiple reaction zone systems are employed in alkylating plants where their use can be justified by the attainment of increased product octane, increased operating flexibility, or increased plant production capacity. Such a plant may have twin reaction zones or even higher multiples of identical reaction zones arranged in a single stage, parallel flow, configuration. The common objective of such a design is to provide higher production capacity in an existing plant or to compensate for size limitations in the ironmongery and unit operations equipment which may be purchased or may be convenient of fabrication. Such a design may also offer the advantage of increased operating flexibility. For example, if it is unavoidable that a plant will receive a varying rate of feed a designer may elect to provide multiple parallel reaction zones whereby the bulk of the processing equipment may be kept in operation and individual reaction zones may be placed in operation or withdrawn from operation as is necessary to compensate for the variation in incoming feed rates. This is a most attractive alternative to cessation of process operation when insufficient incoming feed would cause poor operation of a single, large reaction zone.

Another type of multiple reaction zone system which is in current use is the multiple-stage, series-flow, configuration of reaction zones. It is well known in the art that often multiple consecutive stages of reaction of feeds will produce a superior product to that produced in a single stage of reaction. In such cases the feeds pass through two or more reaction zones in series, contacting an alkylation catalyst in each zone.

A problem shared by prior art multiple reaction zone alkylation processes utilizing hydrogen fluoride arises in the maintenance of the desired quantities and strengths of the acid catalysts within the separate reaction zones. Catalyst is lost from a reaction zone by virtue of its solution within or entrainment by an exiting stream of reaction products. The strength of acid catalyst within a reaction zone will gradually decrease during operation due to the accumulation therein of excess water and polymerized hydrocarbons. Because the rate of decrease of acid quantity or acid strength among the multiple reaction zones may differ quite radically, periodic corrective action is needed to be taken to insure that each zone maintains a sufficient quantity of the proper strength acid catalyst therein. This is particularly important in prior art designs of alkylation processes in which spent catalyst is removed from one reaction zone, regenerated, and returned to a different reaction zone. In such processes it is not uncommon to find that the continuous entry of relatively pure hydrogen fluoride into the receiving reaction zone contributes to a situation of excessive strength of the acid in that zone. As is well known in the art, hydrogen fluoride catalyst of excessive strength, that is, stronger than about 98 wt. % HF, will cause a reduction in process efficiency. When acid strength is increased above the optimum value in a motor fuel alkylation unit, for instance, an increase in the end point of the alkylate boiling range is noted as well as a decrease in the alkylate's octane number. The transfer of acid catalyst from one reaction zone to another for the purpose of controlling acid strength is not new in the art, however it has traditionally been effected through the use of transfer pumps which do not operate continuously, as a rule. Because hydrogen fluoride is an extremely corrosive material when combined with water, as is the case with hydrogen fluoride alkylation catalysts, the transfer pumps traditionally used have been constructed of highly special and very expensive alloy formulations. However, even with the use of these special alloys in the construction of the transfer pumps the maintenance problems involved with their use can be enormous. This has been the case primarily because conventionally used pumps have been of the reciprocating or centrifugal variety, and such pumps contain moving parts which slide across each other while in contact with acid catalyst. This continuous sliding provides, with every sliding action, a fresh metal surface for attack by hydrogen fluoride. In other words, a protective film of oxide is not possible of formation.

Our invention presents an improvement over the prior art by provision of a combination of the well known principal of education with hydrogen fluoride alkylation processes to substantially eliminate the processing problems associated with acid control through the use of pumps in the transfer of acid catalyst from reaction zone to reaction zone.

OBJECTS AND EMBODIMENTS

It is an object of the present invention to provide an improved process for conducting the alkylation of isoparaffins with olefins through hydrogen fluoride catalysis. It is a further object of our invention to provide an improved process for the hydrogen fluoride catalyzed alkylation of aromatics with olefins. A still further object of our invention is to provide improved multiple-reaction zone alkylation processes.

In one embodiment, our invention affords an improved alkylating apparatus of the type in which two or more reactor-settlers are used for the contact of alkylation reactants with alkylation catalysts, wherein the improvement comprises: means for educting catalyst from one of the reactor settlers and means for conducting the educted catalyst to another of the reactor-settlers to control the catalyst inventory and strength within said reactor-settlers.

BRIEF SUMMARY OF THE INVENTION

Our invention involves an improvement in a process for the hydrogen fluoride-catalyzed production of alkylated hydrocarbons using multiple reaction zones. An eductor is used to transfer acid catalyst from any reaction zone having an excess of catalyst or catalyst of excessive strength to any other reaction zone deficient in catalyst quantity or strength. The use of an eductor avoids maintenance problems associated with reciprocating or centrifugal-type pumps in the movement of this catalyst.

BRIEF DESCRIPTION OF THE DRAWINGS

The attached drawings illustrate a particular embodiment of the present invention. Only such details are included as are necessary for a clear understanding of our invention, and no intention is hereby made to unduly limit its scope. Certain items necessary to the operation of the process of this invention but unnecessary to its understanding, such as certain process streams, valves, pumps, instrumentation and other equipment have been omitted for the sake of clarity.

Referring now to FIG. 1, feeds, comprising alkylation reactants, enter reactor 2 in conduit 1 and therein contact a hydrogen fluoride alkylation catalyst. The reaction mixture within reactor 2 passes in conduit 3 to settler 4 where further contact between reactants and catalyst takes place and then settling of the acid phase from the reaction mixture is effected. The settled catalyst phase exits settler 4 in conduit 5 and passes to catalyst circulating pump 14, continuing thenceforth in conduit 5 to reactor 2. A hydrocarbonaceous phase is withdrawn from settler 4 in conduit 6 and is independently intermixed with a stream of olefins entering in conduit 7. The resultant mixture then passes in conduit 6 to reactor 8 where further contact with hydrogen fluoride alkylation catalyst is effected. The reaction mixture within reactor 8 passes in conduit 9 to settler 10 where further contact and, finally, settling of a catalyst phase takes place. The settled catalyst phase exits settler 10 in conduit 12 and passes to catalyst circulation pump 13 from whence it is pumped through a continuation of conduit 12 to reactor 8. A settled hydrocarbonaceous phase, comprising reaction products, exits settler 10 in conduit 11. It should be noted, in the series flow process of FIG. 1, that the combination of reactor 2 and settler 4 comprise a primary reaction zone, and the combination of reactor 8 and settler 10 comprise a secondary reaction zone. It should be noted also that the feeds entering in conduit 1 pass first through the primary reaction zone and then through the secondary reaction zone.

Figure 1:
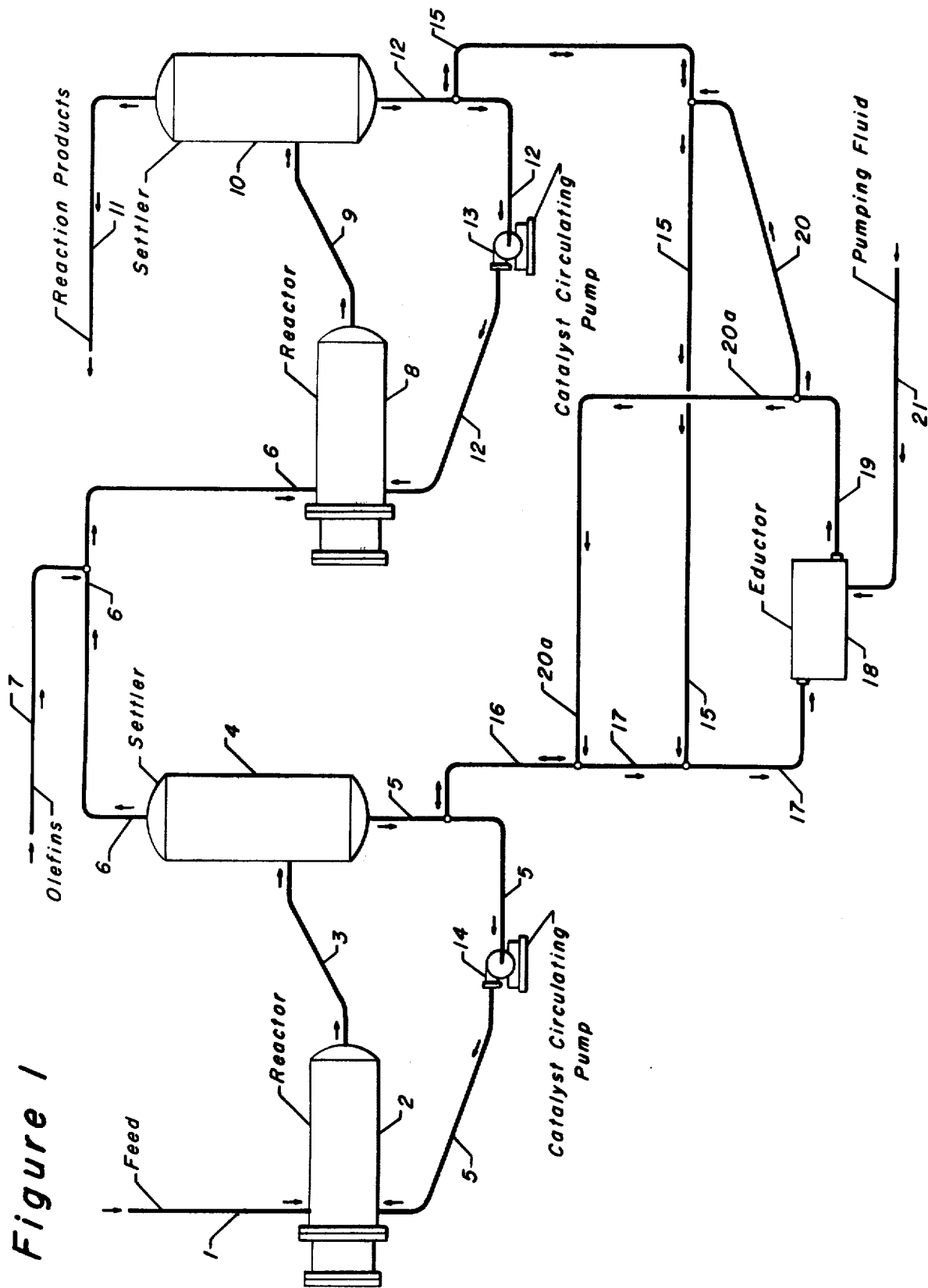
FIG. 1 shows a series flow alkylation process having reactors 2 and 8 and settlers 4 and 10.

Eductor 18 is used for the transfer of a portion of the catalyst within the primary reaction zone to the secondary reaction zone, or vice versa. The motive force for operation of the eductor is provided by a pumping fluid entering the eductor in conduit 21. When eductor 18 is in service, pumping fluid enters in conduit 21 and educts material from conduit 17. The combination of the material from conduit 17 and the pumping fluid then exits eductor 18 in conduit 19.

When it is desired to transfer catalyst from the primary reaction zone to the secondary reaction zone, catalyst is withdrawn from conduit 5 in conduit 16 and is passed to conduit 17. Eductor 18 then withdraws the catalyst from conduit 17 and expulses it into conduit 19. The catalyst so expulsed is conducted within conduit 20 to conduit 15 wherein it is passed to conduit 12, thereby entering the secondary reaction zone.

When it is desired to transfer catalyst from the secondary reaction zone to the primary reaction zone, catalyst is withdrawn from conduit 12 in conduit 15 and is passed to conduit 17. The catalyst is then aspirated from conduit 17 by eductor 18 and passed through conduit 19 into conduit 20a. Conduit 20a conducts the catalyst to conduit 16, through which the catalyst passes enroute to conduit 5. By entering conduit 5 the catalyst enters the primary reaction zone.

Figure 2:
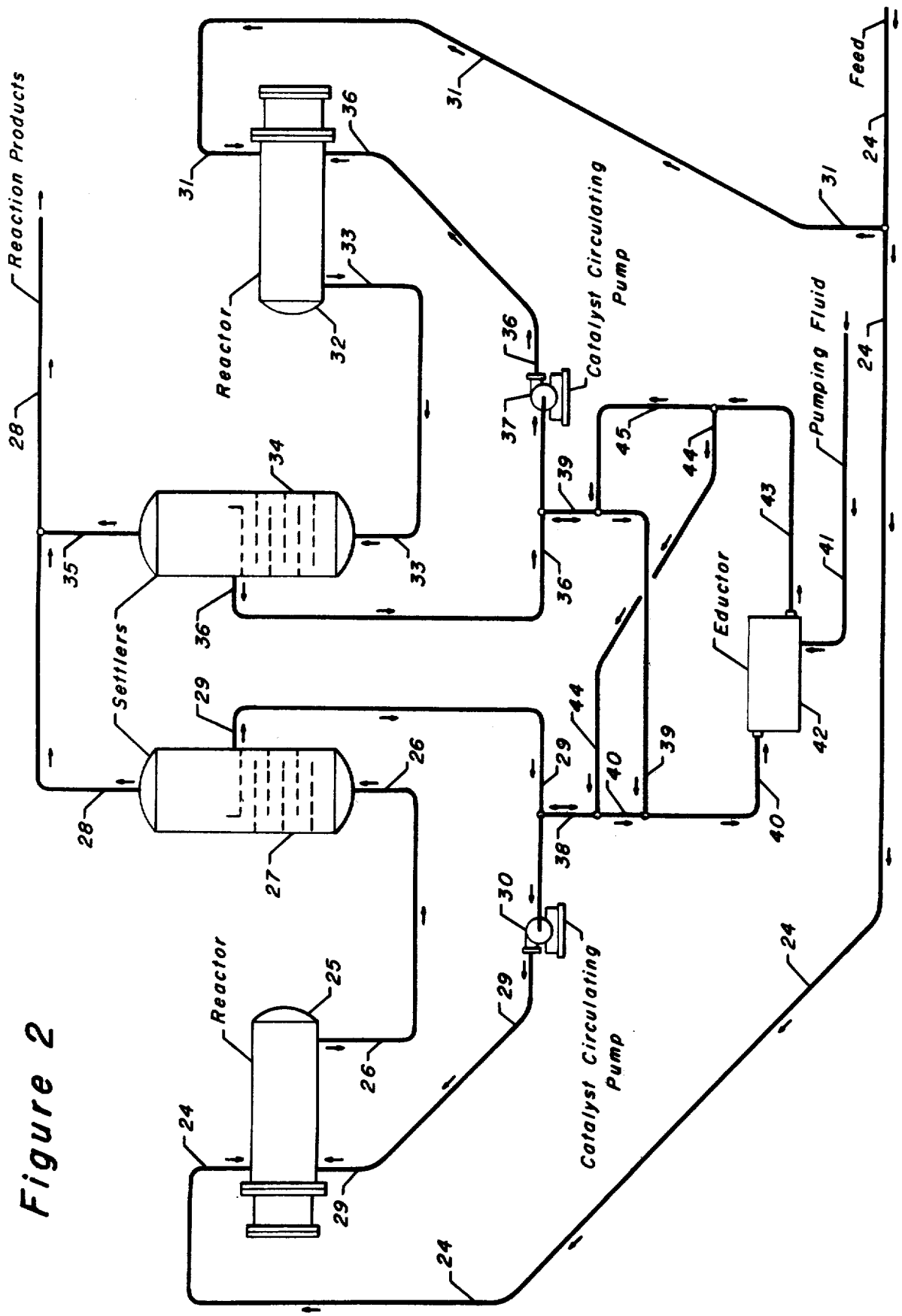
FIG. 2 illustrates a parallel flow alkylation process having reactors 25 and 32 and settlers 27 and 34.

Referring not to FIG. 2, a parallel flow alkylation process is shown wherein feeds entering in conduit 24 divide into two streams, a first stream leaving conduit 24 in conduit 31 and a second stream continuing in conduit 24. The first stream in conduit 31 proceeds to reactor 32 wherein contact is effected between the feeds and a hydrogen fluoride alkylation catalyst. The resultant reaction mixture exits reactor 32 in conduit 33, proceeding to settler 34 where further mixing of the catalyst and feeds is effected and then a catalyst phase is settled from the reaction mixture. The catalyst phase thusly settled exits settler 34 in conduit 36 and passes to catalyst circulating pump 37. The catalyst phase then returns to reactor 32 in a continuation of conduit 36.

The second feed stream in conduit 24 proceeds to reactor 25 and contacts therein a hydrogen fluoride alkylation catalyst. The resulting reaction mixture exits reactor 25 in conduit 26, passing to settler 27. The reaction mixture undergoes further mixing and, later, settling within settler 27, such that a settled catalyst phase may be withdrawn in conduit 29. The settled catalyst phase in conduit 29 passes to catalyst circulating pump 30 and thenceforth continues in conduit 29 to reactor 25.

After withdrawal of the settled catalyst phases from settlers 27 and 34, the remaining portions of the reaction mixtures within the two settlers, comprising hydrocarbonaceous reaction products, are withdrawn. The reaction products from settler 27 are withdrawn in conduit 28 and are joined by a stream of reaction products exiting settler 34 and conduit 35. The combined reaction products from the two settlers exit the process in conduit 28. It should be noted that in the process illustrated in FIG. 2 the feeds have been split into two streams and these two streams have passed through identical reaction zones, each reaction zone being comprised of a reactor and a settler in combination. The reaction products from the two reaction zones have recombined, and this configuration is referred to as parallel-flow.

Eductor 42 is employed to transfer catalyst from one reaction zone to another. When it is desired to transfer catalyst from the reaction zone represented by reactor 25 and settler 27, catalyst is withdrawn from conduit 29 in conduit 38 and passed to conduit 40. Conduit 40 conducts the catalyst to eductor 42 where a pumping fluid within conduit 41 aspirates the catalyst from within conduit 40 and expulses it into conduit 43. From conduit 43 the educted catalyst passes to conduit 45 and then to conduit 39 through which it is conducted to conduit 36. By entering conduit 36 the educted catalyst enters the reaction zone represented by reactor 32 and settler 34.

When the transfer of catalyst is desired to take place from the reaction zone represented by reactor 32 and settler 34 to the reaction zone represented by reactor 25 and settler 27, catalyst is educted from the reactor 32-settler 34 reaction zone by passage from conduit 36 through conduit 39 and into conduit 40 from which eductor 42 aspirates the catalyst. The educted catalyst passes from eductor 42 to conduit 43 and then to conduit 44. From conduit 44 the catalyst enters conduit 38 and passes therein to conduit 29. By entering conduit 29 the educted catalyst from reactor 32-settler 34 enters into the reaction zone composed of reactor 25 and settler 27.

DETAILED DESCRIPTION OF THE INVENTION

Practically all fluid transport which takes place within hydrogen fluoride-catalyzed alkylation processes is motivated by centrifugal force, volumetric displacement, mechanical impulse, or gravity. The selection of pumping means for a particular fluid movement application depends upon many factors including suction and discharge heads and the temperature, viscosity, vapor pressure, and specific gravity of the particular fluid to be pumped. Where hydrogen fluoride-catalyzed alkylation processes are concerned, one of the major fluids to be pumped is hydrogen fluoride, or more specifically alkylation catalysts comprising hydrogen fluoride, water, and hydrocarbonaceous materials. These catalysts usually contain 80 to 98% hydrogen fluoride, hydrocarbonaceous materials and less than 2% water. The corrosive nature of hydrogen fluoride in aqueous solutions of approximately this composition is formidable. Because the major part of all pumping jobs in an HF alkylation process are handled by the use of centrifugal force or mechanical impulse, that is to say, metallic pumping devices utilizing centrifugal impellors or reciprocating pistons, the corrosivity of HF alkylation catalysts has caused us to turn our attention toward use of other means of fluid movement. The use of transfer of momentum as a means of moving fluid is not new in the art. An eductor is a fluid handling device that makes use of the momentum of one fluid to move another. Classically, they have been used for operations where the head pumped against is low and is less than the head of the fluid used for pumping. Educting means are characterized by a pumping fluid, a pumped fluid, and venturi means for imparting to the pumped fluid the momentum of the pumping fluid. Our invention involves a novel combination of the principle of eduction with prior art HF-catalyzed alkylation process principles, which combination results in a greatly improved alkylation process.

Our invention pertains specifically to hydrogen fluoride catalyzed alkylation processes which utilize multiple reaction zones. A reaction zone, as the term is used in the art, commonly comprises a reactor and a settler. The reactor is employed for the intimate admixing and intermingling of reactants with catalyst. A settler then receives the reaction mixture and further mixes it to complete reactions begun in the reactor before finally settling the reaction mixture into a catalyst phase and a reaction product phase. Our invention pertains to HF catalyzed alkylation processes employing such reaction zones in parallel flow or series flow configurations.

Reactants, or feeds as they are sometimes called, which are suitable for use in the alkylation process of our invention may be hydrocarbonaceous compounds such as aromatic compounds, olefinic compounds, and isoparaffinic compounds. Our invention particularly relates to the hydrogen fluoride-catalyzed reaction of aromatics with olefins or isoparaffins with olefins to produce alkylated aromatic compounds or high-molecular weight isoparaffinic compounds, respectively. Materials of particular applicability to our invention are aromatic compounds such as benzene, toluene, xylenes, and the like; isoparaffins such as isobutane, isopentane, isohexane, and the like; and olefins in the $C_3 - C_{20}$ carbon number range.

Our invention is directed toward alkylation processes with multiple reaction zones and solution of a particular problem of such processes. Where multiple reaction zones are employed an imbalance almost invariably occurs, after some period of operational time, in the distribution of alkylation catalyst among the multiple reaction zones. This imbalance may manifest itself as an inequality of catalyst inventory within the multiple reaction zones or a change in catalyst strengths within the various reaction zones. In the process of our invention the principle of eduction is used to great advantage in transferring catalyst from one reaction zone to another reaction zone for the purpose of restoring the catalyst distribution. An important related advantage to the use of educting means is that the intense corrosion problems heretofore experienced in the transfer of HF catalyst by centrifugal or reciprocating pumps is largely avoided. It should be noted, as well, that eduction is of particularly convenient employment here due to the fact that the pumping fluid required for the eductor may be selected from any one of several of the streams which normally are pumped within an HF alkylation process. It is common practice, for example, to recycle from the reaction products back to the reaction zones a stream of unreacted feed components which may be recovered from the reaction products. Because this stream is destined to return to the reaction zone, it is of little consequence, process-wise, that this fluid returns to the reaction zone by way of the educting means instead of directly. It is, however, of great consequence that its route of return to the reaction zone in the process of our invention provides the motive force necessary for educting alkylation catalyst and avoids the necessity of installation of such sources of motive force as electric motors, steam turbines, etc. The use of an olefin-bearing stream is, of course, prohibited, due to the formation of high-molecular weight polymers which would follow upon the contact of such a stream with hydrogen fluoride alkylation catalyst. However, practically any of the other streams normally encountered in an alkylation process may be used. It should be remembered in the choice of a pumping fluid that the pumping fluid will become admixed with the pumped fluid in operation of the eductor. Also, the stream chosen for use as pumping fluid should be compatable with the reaction mixture found within the reaction zone. We prefer to use as a pumping fluid either a portion of the recycle stream of unreacted feed components which have been separated from reaction products, the pump fish stream which is commonly found in HF alkylation units, or bottoms streams from such downstream fractionating zones as depropanizing zones or HF stripping zones which are commonly found in HF alkylation processes. All of the aforementioned streams are commonly encountered under sufficient pressure to afford the head necessary to accomplish the educting job at hand.

In the multiple reaction zone, HF-catalyzed alkylation process of our invention, whether arranged in a parallel or a series flow configuration, educting means are provided for the removal of alkylation catalyst from any one of the reaction zones and conducting means are provided for the conduction of the catalyst so educted to any of the other reaction zones. A single educting device is sufficient, regardless of the number of reaction zones employed in the process, provided that the conduits involved in conduction of the catalyst are arranged with the proper valving so that the educting means may be connected on its suction side to any one reactor and on its discharge side to any other reactor in the system. This may be facilly accomplished in any one of a number of different ways, one of which is shown in the accompanying drawing. In brief, the suction side of the educting means is connected by individual conduits to each reaction zone at a point where acid catalyst may be withdrawn. Means for conducting educted catalyst to reaction zones is likewise easily accomplished by the provision of a set of individual conduits, each individual conduit leading from the discharge side of the educting means to an individual reaction zone in the process. It should be noted that the installation of valves within each of the aforementioned individual conduits will be necessary in order to be able to isolate the suction side conduit and the discharge side conduit which are necessary in a particular set of circumstances for the transfer of catalyst as desired. In other words, it will be necessary to provide an open connection from the suction side of the ejecting means only to that reaction zone from which it is desired to withdraw catalyst, and to provide an open connection from the discharge side of the educting means only to that reaction zone to which it is desired to conduct the educted catalyst. That is to say, the valves within the conduits in use will be open and the valves within the conduits which are not desired to be used will be closed. By way of illustration, in FIG. 1 it would be necessary to install valves in each of the following conduits; conduit 20, conduit 20a, conduit 15, and conduit 17 (between the connection of conduit 17 with conduit 15 and the connection of conduit 17 with conduit 20a). In the process of FIG. 2 it would be necessary to install valves at the following locations: conduit 45, conduit 44, conduit 39 (between its connection with conduit 45 and its connection with conduit 40), and conduit 40 (between its connection with conduit 39 and its connection with conduit 44).

Continued operation of a reaction zone results in the accumulation, within the acid catalyst phase, of contaminating components and a resultant decrease in the activity of the catalyst therein. Where multiple reaction zones are arranged in a series flow configuration, the catalysts within the individual reaction zones may deactivate at different rates. Referring to the process shown in FIG. 1, the feeds entering in conduit 1 pass first through the reaction zone represented by reactor 2 and settler 4, where the action of the acid catalyst therein upon the active species in the feeds consumes these reactive species and produces not only desired alkylate products but also undesirable byproduct compounds which contaminate the acid catalyst. The reaction mixture exits settler 4 of the first reaction zone in conduit 6, and reactant species therein are replenished by a stream of olefins entering in conduit 7. It might be suspected that with this replenishment of the active species the two reaction zones would be working at about the same level of exertion. However, it is often found that the acid catalyst in the primary reaction zone deactivates at a higher rate than the catalyst in the secondary reaction zone. In such a case the concentration of hydrogen fluoride within the acid catalyst in the primary reaction zone decreases, over a period of time, at a greater rate than the like decrease taking place in the secondary reaction zone. When the catalyst strength in the primary reaction zone reaches a prohibitively low level it is desirable to educt catalyst of greater strength, that is, catalyst of higher hydrogen fluoride content, from the secondary reaction zone and conduct it to the primary reaction zone. Conversely to the aforementioned situation, a situation where catalyst becomes too strong can arise. This may happen, for instance, where an acid regenerating scheme is put into operation and the influx into a reaction zone of freshly regenerated acid is enough to cause the concentration of hydrogen fluoride within the acid catalyst to exceed desired levels. If this were the case in the process shown in FIG. 1 and the secondary reaction zone contained a catalyst which had become too strong then it would be desirable to educt weaker catalyst from the primary reaction zone and conduct it to the secondary reaction zone to dilute the overly-strong acid catalyst therein.

Where parallel flow configurations of multiple reaction zones are employed, it is often necessary or desirable to vary the amount of feeds entering the individual reaction zones. That is to say, one reaction zone may be processing feeds at a rate equal to its maximum capacity while another reaction zone may be processing feeds at a significantly lower rate. In such a case the reaction zone processing higher rates of feeds will suffer a more rapid catalyst deactivation rate. If the catalyst strength in such a reaction zone is decreased to a prohibitively low level then it will be desirable to introduce catalyst of higher strength which has been educted from one of the other reaction zones.

FIG. 1 will be referred to in the explanation of examples of the operation of the process of our invention while operating reaction zones in series flow to produce either high octane isoparaffins or alkylated aromatic compounds. Feeds, comprising either aromatic compounds such as benzene, toluene, and xylene, or isoparaffins such as isobutane and isopentane, enter the process in conduit 1 and contact hydrogen fluoride alkylation catalyst in the primary reaction zone which is represented by reactor 2 and settler 4. The hydrocarbonaceous reaction products from the primary reaction zone exit in conduit 6, are mixed with a replenishing stream of olefins from conduit 7, and proceed to the secondary reaction zone which is represented by reactor 8 and settler 10. After contact of the reaction mixture with the acid catalyst in the secondary reaction zone, a hydrocarbonaceous reaction product exits the process in conduit 11. The acid catalyst within the primary reaction zone, which catalyst is being recirculated from the settler 4 through conduit 5 and catalyst circulating pump 14 becomes deactivated such that a decrease in the efficiency of the primary reaction zone is noted. The acid catalyst circulating within the secondary reaction zone from settler 10 through conduit 12 and catalyst circulating pump 13 to reactor 8 is chemically analyzed and found to be of greater strength than the acid catalyst in the primary reaction zone. In order to increase and control the strength of the primary reaction zone's catalyst, acid catalyst from the secondary reaction zone is withdrawn in conduit 15 and aspirated into eductor 18 through passage from conduit 15 into conduit 17 and thenceforth into the eductor. A pumping fluid, selected from the available pressurized streams within the process, is introduced into the eductor at a rate sufficient to aspirate the catalyst from the secondary reaction zone and to transfer the catalyst to the primary reaction zone through the following flow path: conduit 19 to conduit 20a to conduit 16 to conduit 5. If it is necessary to transfer catalyst in the reverse direction, that is, from the primary reaction zone to the secondary reaction zone the following flow path is utilized: catalyst is withdrawn from conduit 5 in conduit 16 and passes to conduit 17 through which the catalyst is aspirated into eductor 18. Catalyst so educted is expulsed into conduit 19 from which it enters conduit 15 and passes to conduit 12 of the secondary reaction zone.

Reference will now be made to FIG. 2 in the explanation of examples of operation of the process of our invention in the parallel-reaction zone configuration. The mode of utilization of the catalyst transfer feature of our invention is identical whether the feeds being processed are aromatics and olefins or whether they are isoparaffins and olefins. Feeds entering in conduit 24 are split into a first and a second stream, the first is equivalent to one-half of the design capacity of the reaction zone represented by reactor 32 and settler 34. This stream enters that reaction zone in conduit 31 and contacts hydrogen fluoride alkylation catalyst therein. The second stream of feeds continues in conduit 24 and enters the reaction zone represented by reactor 25 and settler 27. The feed stream in conduit 24 is equivalent to 100% of the design capacity of its associated reaction zone. Hydrocarbonaceous reaction products from settler 27 and settler 34 combine in conduit 28 and exit the process. The passage of a higher rate of feed through the reactor 25-settler 27 reaction zone causes a higher loss of acid catalyst therefrom. This is due to the catalyst which leaves the reaction zone in solution and entrained by the feeds passing therethrough. The greater physical loss of acid catalyst from reactor 25-settler 27 than from reactor 32-settler 34 causes the inventory of catalyst within reactor 25-settler 27 to become depleted to a prohibitive extent. In order to replenish the depleted inventory of catalyst in the reaction zone of higher throughput acid catalyst is withdrawn from conduit 36 of the reaction zone of lower throughput in conduit 39 and is passed to the suction side of eductor 42. Pumping fluid enters the eductor in conduit 41 and aspirates the acid catalyst from conduit 40, expulsing it into conduit 43. From conduit 43 the educted catalyst is conducted through conduit 44 and into conduit 38 from whence it is discharged into conduit 29 of the higher-throughput reaction zone. If it should be desired to transfer in the reverse, that is from the reactor 25-settler 27 reaction zone to the other reaction zone the following flow path is used: acid catalyst is withdrawn from conduit 29 in conduit 38 and passed to conduit 40 from which it is educted by eductor 42 and expulsed into conduit 43. From conduit 43 the catalyst is conducted through conduit 45 and into conduit 39 which discharges the catalyst into conduit 36 of the reactor 32-settler 34 reaction zone.

The following is an example in which continuous regeneration of hydrogen fluoride alkylation catalyst caused an overabundance of both catalyst quantity and catalyst strength within a primary reaction zone of a series flow process. As aforesaid, it is not uncommon to find alkylation process designs in which catalyst is continuously withdrawn from the secondary reaction zone of the process and regenerated to produce relatively pure hydrogen fluoride which is reintroduced into the primary reaction zone. Variations in processing conditions can cause a decrease in the rate of catalyst deactivation within the primary reaction zone. An example of such a situation might be a period of low feed rate operation. In such a case catalyst of excessive strength can accumulate in the primary reaction zone to levels of inventory which are undesirable. In such cases the eductor and conducting means of our invention are used to transfer, much like the above examples, a portion of such accumulated acid catalyst from the primary reaction zone to the secondary reaction zone.

The above examples are not meant to be the only occasions for the use of our invention and no intention is hereby made to unduly limit its scope.

We claim as our invention:

1. An alkylating apparatus comprising a first reactor and a first settler communicating therewith, a second reactor, a second settler communicating with the second reactor, means for passing liquid from the upper portion of the first settler to the second reactor, a first catalyst recirculating conduit between said first settler and said first reactor, a second catalyst recirculating conduit between said second settler and said second reactor, an eductor, first conduit means connecting said first recirculating conduit with the inlet end of said eductor, second conduit means connecting the outlet end of the eductor with said second recirculating conduit, an additional conduit connecting said second conduit means with said first conduit means, and a separate conduit connecting said second conduit means with said first conduit means, whereby said additional conduit and said separate conduit provide means by which catalyst may be moved from said first catalyst recirculating conduit to said second catalyst recirculating conduit, or vice-versa, to enable selective adjustment of the catalyst inventory in the first and second reactor-settler circuits.

* * * * *